United States Patent [19]

Leiman et al.

[11] Patent Number: 4,879,999
[45] Date of Patent: Nov. 14, 1989

[54] DEVICE FOR THE DETERMINATION OF PROPER ENDOTRACHEAL TUBE PLACEMENT

[75] Inventors: Basil C. Leiman; Bruce D. Butler; Jeffrey Katz; Henry H. Salzarulo, all of Houston, Tex.

[73] Assignee: Board of Regents, The University of Texas System, Austin, Tex.

[21] Appl. No.: 58,830

[22] Filed: Jun. 5, 1987

Related U.S. Application Data

[63] Continuation of Ser. No. 844,090, Mar. 26, 1986, abandoned.

[51] Int. Cl.$^4$ .............................................. A61M 16/00
[52] U.S. Cl. ........................... 128/207.14; 128/202.72; 128/419
[58] Field of Search ....................... 128/200.26, 202.22, 128/205.23, 207–207.16, 656–658, 716, 719; 116/200, 201, 206, 209; 604/280; 422/55–59, 61, 84–89, 103, 104; 436/133

[56] References Cited

U.S. PATENT DOCUMENTS

| 2,638,096 | 5/1953 | Waldhaus | 128/207.14 |
| 2,904,033 | 9/1959 | Shane | 128/205.23 |
| 4,346,584 | 8/1982 | Boehringer | 128/719 |
| 4,366,821 | 11/1983 | Wittmaier | 128/719 |
| 4,691,701 | 9/1982 | Williams | 128/207.14 |
| 4,728,499 | 3/1988 | Fehder | 422/85 |
| 4,790,327 | 12/1988 | Despotis | 128/207.16 |

OTHER PUBLICATIONS

Advertisement for End-Tidal $CO_S$ Detector.
"A pH-Sensitive Device Detects Inadvertent Esophageal Intubation", Anesthesiology News, September, 1988.

Primary Examiner—Kyle L. Howell
Assistant Examiner—K. M. Reichle
Attorney, Agent, or Firm—Arnold, White & Durkee

[57] ABSTRACT

Disclosed is an endotracheal device provided with a colorimetric carbon dioxide indicator. The device functions to indicate the proper intratracheal placement of an endotracheal tube by detecting for the presence of carbon dioxide in expired air passing through the device.

26 Claims, 3 Drawing Sheets fig. 9 fig. 8

DEVICE FOR THE DETERMINATION OF PROPER ENDOTRACHEAL TUBE PLACEMENT

This application is a continuation of application Ser. No. 844,090, filed Mar. 26, 1986, now abandoned.

BACKGROUND OF THE INVENTION

1. Field of the Invention

The present invention relates to improved endotracheal tubes and devices for use in conjunction with such tubes. More particularly, the present invention is directed to endotracheal tubes which employ a carbon dioxide indicator to determine proper placement of the tubes in the trachea.

2. Description of the Relevant Art

Accidental undetected esophageal intubation remains a major cause of anesthetic death and disability. In the anesthetized, paralyzed patient, as well as in the victim of injury or illness, an endotracheal tube is placed to secure the airway, permit controlled ventilation, and prevent the risk of vomiting with the aspiration of gastric contents. Ventilation of the lungs is essential to life. It is the mechanism by which oxygen is carried into the body and carbon dioxide, a constant product of metabolism, is eliminated. The apneic patient, whether as a result of anesthesia, cardiac arrest, injury, respiratory failure or airway obstruction must be artificially ventilated in order to survive. Unfortunately during the attempted endotracheal intubation, the esophagus is sometimes accidentally intubated. If this error is detected quickly, no damage results. However, if this condition is permitted to persist for even a few minutes, brain injury and death occur.

The laryngoscopist attempts to pass the endotracheal tube into the tachea under direct vision. Unfortunately, this is not always possible. Routine measures to confirm proper tube placement include visual inspection of the chest, ausculation of the chest and upper abdomen, observation of the endotracheal tube for condensation during expiration, use of EKG, precordial and esophageal stethoscopes, and frequent monitoring of vital signs. In spite of these measures, undetected esophageal intubations continue to occur with the predictable disastrous results.

Confirmation of proper tube placement can be based upon the fact that carbon dioxide, a product of metabolism, is always present in exhaled air in approximately 5% concentration, but is present in esophageal gas in only minute concentrations. The capnograph and mass spectrometer are two instruments which have gained limited use in the operating room to detect proper endotracheal tube placement. Both depend upon the presence of carbon dioxide to make the determination. However, both are expensive instruments, beyond the budget of many hospitals and unavailable at the scene of an accident or cardiac arrest, in the ambulance, or the emergency room. Additionally, both are subject to calibration errors and in the case of the mass spectrometer, there may be an intolerably long delay before the carbon dioxide tension is determined.

A third device, the "Einstein $CO_2$ Detector" was described in. Berman et al. (1984). *Anesthesiology*, 60: 613-614. The Einstein Detector utilizes a deLee mucus trap containing an aqueous colorimetric carbon dioxide indicator in line with an endotracheal tube. Unfortunately, the Einstein $CO_2$ Detector has failed to gain even limited acceptance for it is messy, time consuming, and requires that the detector be disconnected from the breathing circuit before air can pass bidirectionally through the endotracheal tube. Clearly, then, the ideal $CO_2$ detector has not yet arrived on the health care scene.

This ideal detector should be inexpensive, reliable, and simple. It should not require, nor be subject to errors of calibration. It should be capable of being incorporated into the endotracheal tube or breathing circuit so that disconnection is unnecessary and so that it will not add to the burgeoning assortment of equipment and instrumentation already threatening to choke the operating room and topple the anesthesia machine. At the scene of accidents or heart attacks, where conditions are difficult and the laryngoscopist likely to be less experienced, the need for a reliable, self-contained $CO_2$ detector is great.

SUMMARY OF THE INVENTION

Recognizing the need for an improved endotracheal tube, it is a general object of the present invention to provide a novel endotracheal device which minimizes or reduces the problems of the type previously noted.

The invention, in a general aspect, concerns an endotracheal device having the ability to indicate proper intratracheal placement of the device. The device is inexpensive, easy to use and is accurate in its determinations. Its manner of use involves the detection of $CO_2$.

The devices or apparatus of the invention may be individually packaged and pre-sterilized, thereby rendering them usable directly in the "field,"—e.g., at the scene of an accident—without the need for further sterilization. The device, when properly prepackaged and presterilized, is ready for immediate use.

The invention in a general sense comprises a tubular housing which defines a lumen for the bidirectional passage of air into and out of a patient's trachea. The interior or luminal surface includes a carbon dioxide indicator which is capable of detecting the passage of carbon dioxide through the housing.

In a preferred form the housing is tubular and has a first and second end. The first end is adapted for insertion into a trachea, where upon air is able to pass through the housing bidirectionally. Preferably, suitable means are attached to the housing in communication with air passing therethrough for detecting the presence of carbon dioxide in the air. The detection means preferably comprises a colorimetric carbon dioxide indicator.

Endotracheal devices made in accordance with the present invention may comprise a single tubular housing with a carbon dioxide indicator adhered to, absorbed onto, incorporated in, fixed to, or otherwise communicating with the tubular housing in such a matter so as to communicate with air passing through the housing.

Alternatively, the endotracheal device of the present invention may be embodied in two separate housings. A first such housing is tubular with first and second ends, and defines a lumen for passing air into and out of a trachea. The second such housing is attached to the first tubular housing, and is adapted to communicate with air passing out of the trachea. The second housing includes a colorimetric carbon dioxide indicator.

The device of the invention may be made and marketed as an integral unit. However, it may also be made and marketed as components capable of being assembled. For example, the components may include an endotracheal tube; a housing attachable to the tube for communicating with air passing through the tube; and a colorimetric carbon dioxide indicator to be used in the housing. Expressed otherwise, the advantages of the invention may be attained by providing and using a housing which contains a carbon dioxide indicator with an endotracheal tube in such a way as to determine the proper placement of the tube in a patient's trachea. It is essential that the housing containing the carbon dioxide indicator be positionable such that the indicator is able to communicate with air passing through the tube, and thereby be capable of detecting the presence of carbon dioxide in the air. It is also important that the tube be able to pass air through the tube bidirectionally.

It is further important that the various components and assemblies of the device of the present invention be provided in a sterile condition. Thus, it is contemplated that such components and assemblies will normally include a special sterilized wrapper for maintaining the components and assemblies in a sterile condition, once sterilized.

DETAILED DESCRIPTION OF A PREFERRED EMBODIMENT

Figures 1, 2, 3:
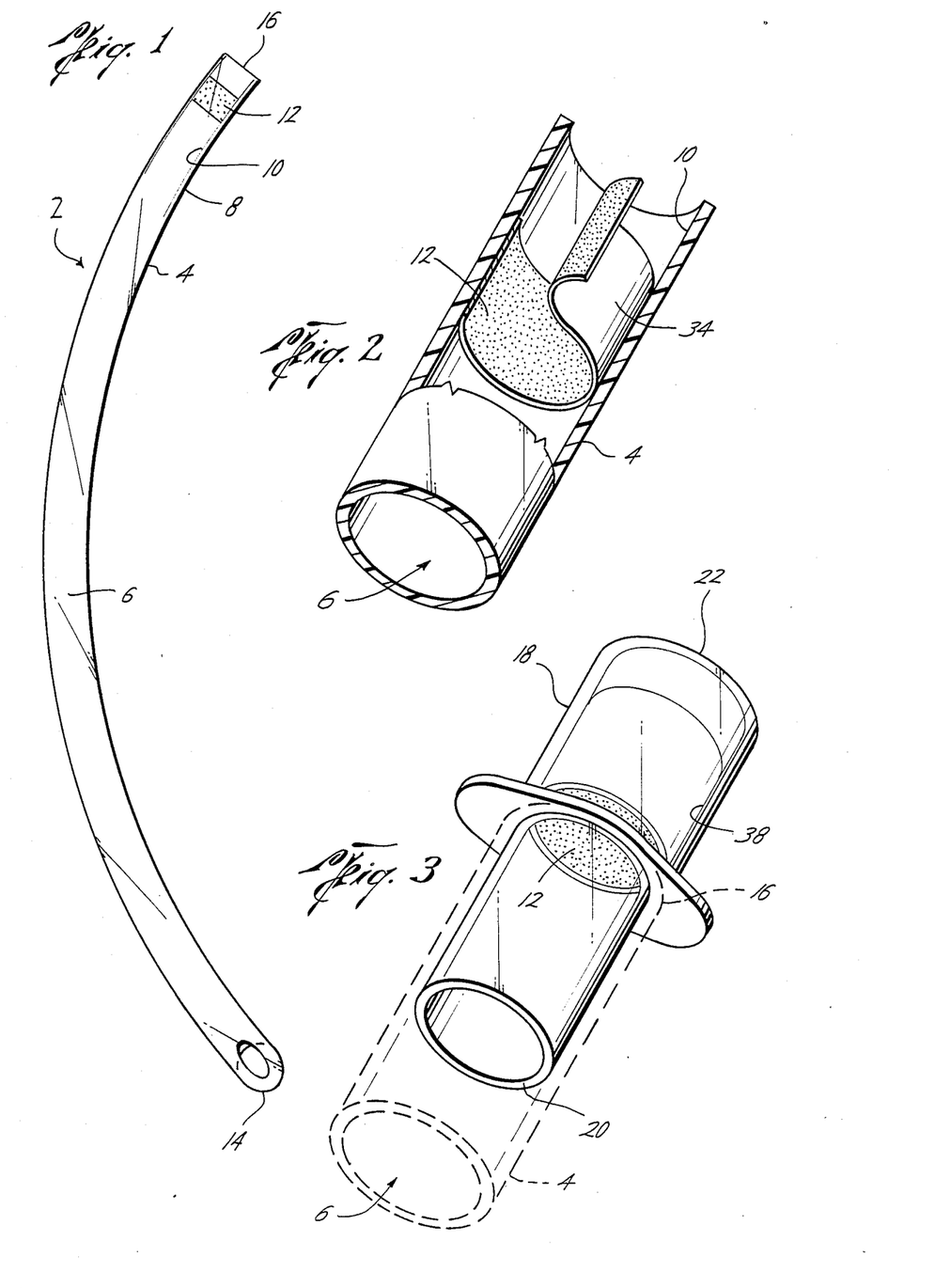
FIG. 1 is a full view of an endotracheal device which illustrates a general embodiment of the present invention.
FIG. 2 is a perspective, partially cutaway view of the embodiment of FIG. 1 showing one means of adhering the carbon dioxide indicator to the luminal surface of an endotracheal device.
FIG. 3 is a perspective view, partially in phantom, which illustrates the attachment of a tubular connector or secondary housing which contains the carbon dioxide indicator, to the proximal end of an endotracheal tube.

FIG. 1 illustrates a general embodiment of the present invention. Displayed there is a device 2 for maintaining an open bidirectional air passage in a patient's trachea. The device has a tubular housing 4 which defines a lumen 6, and which has an external surface 8 and a luminal surface 10. A carbon dioxide indicator 12 is applied or adhered to, or is otherwise part of the luminal surface 10. The tubular housing 4 further includes a first end 14, also referred to as a distal end, and a second end 16, also referred to as a proximal end. The lumen 6 extends between the ends 14 and 16.

FIG. 2 demonstrates one means for adhering a carbon dioxide indicator 12 to the luminal surface 10 of FIG. 1. As displayed there, a clear or translucent backing member 34 having the indicator 12 adhered to one side of the backing member and a bonding agent adhered to the otherside, may be used to bind the indicator to the luminal surface.

FIG. 3 shows a typical tubular connector or secondary housing 18, adapted for attachment to the proximal end 16 of the tubular housing 4. The housing 18 will typically have an exposed end 22 and an attachment end 20 allowing attachment of the housing 18 to the tubular housing 4 (shown in phantom). The exposed end 22 may be further adapted to connect to additional tubular structures where desired. The carbon dioxide indicator 12 is adhered to the luminal surface 38 of the housing 18 and communicates with air passing bidirectionally through the lumen 6 of the tubular housing 4.

Figure 4:
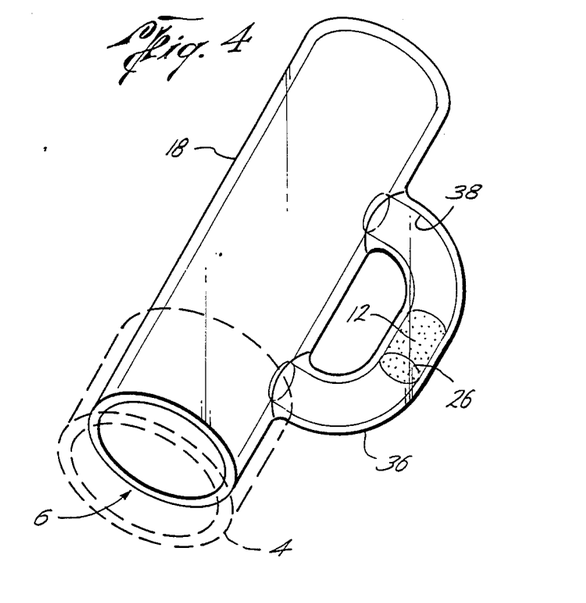
FIG. 4 is a perspective view of a tubular connector having a shunt channel.
Figure 5:
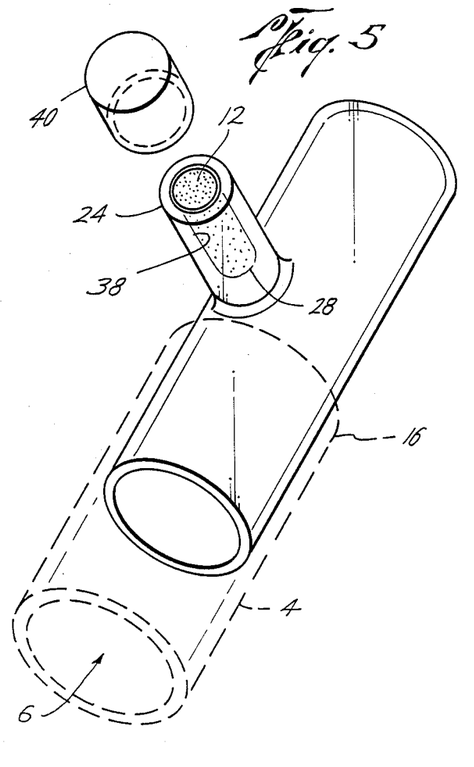
FIG. 5 is a perspective view of a connector having a side-arm.

FIGS. 4 and 5 illustrate alternative embodiments to the placement of the indicator 12 in the primary luminal path 6. In connector or secondary housing 18 of FIG. 4, the indicator 12 is adhered or adsorbed onto a solid support 26 and placed into a shunt or secondary lumen or channel 36. Although FIG. 4 places the secondary lumen in a connector or secondary housing 18, which is attachable to an endotracheal tube or primary housing 4, it is clear that the secondary lumen may also be incorporated directly in the tubular housing 4.

In FIG. 5, the alternative lumen 28 is defined by a side arm 24. The side arm 24 may be provided with a removable cap 40 to allow testing for the presence of $CO_2$ in expired air at selected times. Thus, when such cap 40 is removed, air is vented through the side arm and thereby communicates with the $CO_2$ detector 12 in the side arm 24.

Figure 7:
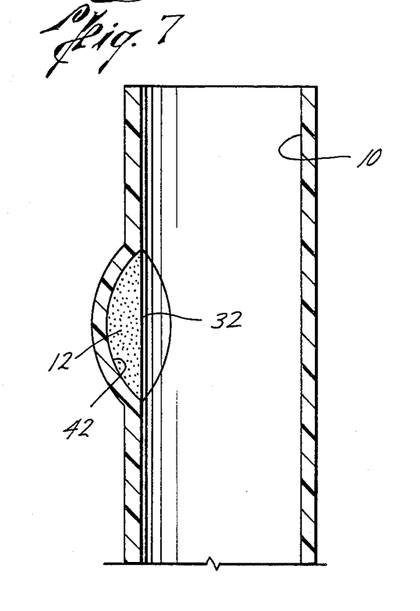
FIG. 7 is a longitudinally sectioned view of a recessed-wall configuration for retaining the carbon dioxide indicator.

Alternatively, as displayed in FIG. 7, the $CO_2$ indicator may be placed into recessed well 42 in a lumen 6, and thereby continuously communicate with air passing through such lumen.

Figure 6:
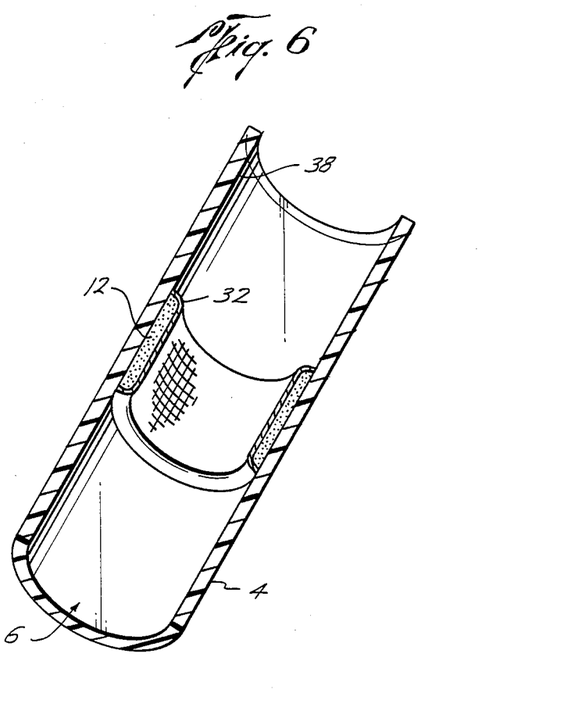
FIG. 6 is a perspective, longitudinally sectioned view showing a carbon dioxide indicator adhered to a luminal surface with a gas permeable membrane.

In certain embodiments of the invention, it may be desirable to employ a gas permeable membrane such as element 32 in FIG. 6. Such membranes may be employed both as a means of adhering the indicator 12 to the luminal surface 10, and as a means of retaining potentially toxic substances. Air passing through the lumen 6 in FIG. 6 can contact the carbon dioxide detector 12 through the membrane 32, but there is no danger that the detector material, itself, can enter the air stream.

The present invention permits immediate and proper endotracheal tube placement, as well as confirmation of such placement, without additional expense or equipment and without the need to disconnect a breathing circuit. In its most basic embodiment, a sensitive carbon dioxide indicator is brought into contact with exhaled air. The indicator may sense a pH change, a heat change, or may directly detect $CO_2$. A pH change occurs when $CO_2$ reacts with water ($H_2O$) to form carbonic acid ($H_2CO_3$). Hydrogen ions from the reaction then react with a color indicator, for example a redox indicator, to produce a color change which is visible to the human eye. Thus, when a colorimetric reaction takes place, the presence of carbon dioxide in expired breath is indicated. Similarly, carbon dioxide reactions may react with a heat sensitive indicator to yield the desired colorimetric change. Therefore, it is contemplated that temperature-sensitive indicators which change color in the presence of a pre-determined temperature change (e.g., Temp-A-strip, Sharn, Inc., Tampa, Fla.) may be used to indicate the presence of carbon dioxide in expired gases.

Moreover, indicators which react with the bicarbonate ion ($HCO_3^-$), or which react directly with carbon dioxide, may be utilized to yield a colorimetric indication. In general, any colorimetric carbon dioxide indicator substance which is capable of producing the desired colorimetric change in the presence of air having approximately 5% carbon dioxide, may be utilized in the practice of the present invention.

The fact that the present invention incorporates a colorimetric carbon dioxide indicator, allows for quick visual determination that carbon dioxide is present in the gases flowing through the lumen of an endotracheal device, thus indicating the proper placement of the device within the trachea. In a preferred reaction, carbon dioxide combines with hydrazine, soda lime, sodium hydroxide, calcium hydroxide or barium hydroxide, thereby providing a pH change which may be detected by a colorimetric pH indicator, for example, 2,4 dinitrophenol, ethyl violet, crystal violet, methyl orange, benzopurpurin, ethyl red, or alizarin sodium sulfate. Additionally, baralyme, which typically consists of 80% calcium hydroxide with 20% barium hydroxide added as an activator, has been used in the absorption of carbon dioxide; accordingly, it is contemplated that this material will also function as a $CO_2$ indicator when compounded with a suitable colorimetric pH indicator. Numerous colorimetric pH indicators are known in the art and may be utilized in the practice of the present invention.

In a preferred embodiment of the present invention, a carbon dioxide indicator containing hydrazine in combination with a typical redox indicator, such as crystal violet, is employed. Carbon dioxide reacts with hydrazine to form carbonic acid monohydrazide which discolors the redox indicator. This indicator, which has been found to function well in the practice of the present invention is obtained from Gastec Corporation, Yokohama, Japan and is identified as Gastec carbon dioxide high range detection tube 2H. However, all of the Gastec carbon dioxide detection granules have been found to function properly in the practice of the present invention.

In another preferred embodiment, a "dry" carbon dioxide indicator is utilized. A dry indicator is preferable in that it eliminates the complaint that it is messy and inconvenient. Additionally, dry carbon dioxide indicators are generally more stable over longer periods of time and may be more easily sterilized to provide prepackaged, sterile endotracheal devices in accordance with the present invention. However, it is contemplated that wet carbon dioxide indicators may be utilized where the indicator is either adsorbed onto a solid support or otherwise brought into communication with air passing through the device in such a manner so as to allow air to pass bidirectionally. The requirement that air be allowed to pass through the device bidirectionally allows for carbon dioxide indication without, for example, connecting and then disconnecting a carbon dioxide indicator housing. However, the carbon dioxide indicator may be located so as to come in contact with only exhaled air by providing one luminal passage for expired breath and a second luminal path for inspired breath, the carbon dioxide indictor being located to communicate with only the expired air.

In a basic embodiment, the indicator is painted or adhered to the inside wall of the endotracheal tube, or other device utilized to provide an open air passage into a patient's trachea. In the illustrative embodiment of Example I below, it is demonstrated that double-sided adhesive tape suffices as a means to adhere the $CO_2$ indicator to the inside or luminal wall of the device. However, all methods of adherance, including but not limited to, gluing, bonding, absorbing, adsorbing, epoxying and suspending onto are considered to be within the scope of the present invention. It is especially contemplated that the indicator may be incorporated onto the luminal surface of such a tube during its manufacture.

Figure 8:
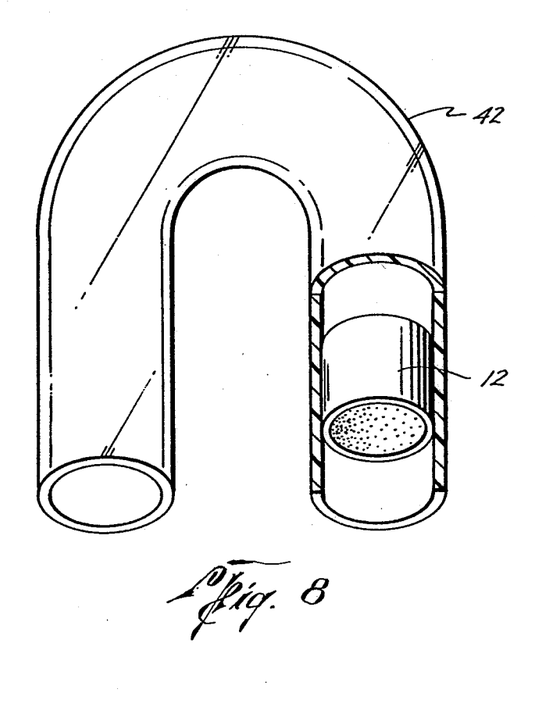
FIG. 8 is a perspective view of various connectors.
Figure 9:
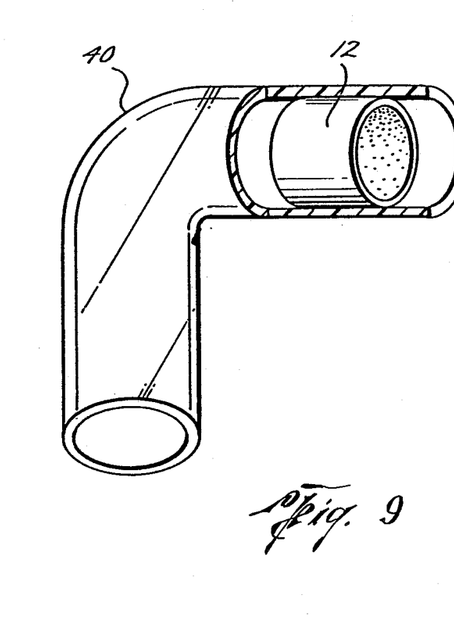

In a further embodiment, the carbon dioxide indicator may be adhered to, or incorporated into, a housing adapted to attach to the proximal end of the endotracheal device. Once the housing is attached to the proximal end of the endotracheal device, the distal end of the device may be inserted into the trachea. Alternatively, the patient may be first intubated followed by attachment of the carbon dioxide indicator/housing to the proximal end of the endotracheal device, to determine if the device was properly placed within the patient's trachea. The indicator housing may take the form of any one of a number of connectors well-known in the art; suitable connectors include but are not limited to elbow joints 40 (FIG. 8), u-joints 42, in line connectors, or any other such fittings, or devices capable of communicating with air passing therethrough.

As previously discussed in connection with FIG. 6, it may be desirable to provide a gas permeable membrane over the carbon dioxide indicator to secure the indicator in place or to enable the use of wet carbon dioxide indicators. In the case of wet indicators, the membrane will retain the wet indicator within the luminal air path without obstructing the flow of air. The gas permeable membrane may be Teflon, Cellophane, polyethylene, polypropylene or other membrane substances known to the art. It may also be desirable in some applications to adsorb the carbon dioxide indicator onto an inert support such as cellulose, cotton, glass beads, calcium carbonate or silica. Alternatively, solid supports may be employed which actually contribute to the colorimetric carbon dioxide detection reaction. For example, as discussed above, one type of well-known carbon dioxide detection reaction utilizes a redox or pH indicator in connection with soda lime (which is a mixture of calcium hydroxide with sodium, potassium or barium hydroxide in general use for the absorption of carbon dioxide gas and water vapor). The combination of the soda lime with the colorimetric redox or pH indicator functions as a colorimetric carbon dioxide indicator.

The solid supports discussed above are useful in that they provide an alternative to adhering the carbon dioxide indicator to the luminal surface. For example, the solid supports may conveniently be placed in the sidearm 24 of FIG. 5, the alternative lumen 36, 28 of FIGS. 4 or 5, respectively, or retained within the gas permeable membrane 32 of FIG. 6. In each such embodiment, it is contemplated that the solid support/carbon dioxide indicator will function to achieve the objectives of the present invention.

EXAMPLE I

An 8 cm longitudinal slit was made in the proximal end of a transparent endotracheal tube. A band of transparent double sided adhesive tape was then stuck circumferentially around the inside of the tube, approximately four centimeters from the proximal end. Granules obtained from a Gastec carbon dioxide high range detection tube 2H were then sprinkled onto the intraluminal side of the adhesive tape to create a uniform layer. The slit was then closed and sealed with transparent adhesive tape.

Human Experimentation

Four adults participated in this study. Each subject completed 2 experiments. The subjects inhaled room air deeply, and then placed the distal end of the carbon dioxide detector/endotracheal tube into their mouth following which they exhaled through the tube. In all cases, the band containing the $CO_2$ detector changed from white to violet with the first exhaled breath.

Animal Experimentation

Anesthesia was induced in 2 mongrel dogs (20-24 kg) with thiopentone (25 mg/kg) and, following endotracheal intubation (with a regular endotracheal tube), anesthesia was maintained with halothane 1.5% in oxygen.

Succinylcholine at 0.5 mg/kg was then injected to produce muscle relaxation (paralysis). The animals were ventilated using a Harvard animal ventilator at a rate of 12 breaths per minute. Each dog was then extubated and the esophagus intubated with a $CO_2$ detector endotracheal tube. The ventilator was connected to the endotracheal tube for a period of 6 breaths. No color change was noted upon observation for color change in the $CO_2$ detector granules. Following this, the trachea was intubated using the carbon dioxide detector tube and the color change was noted. In all 4 experiments in which the trachea was intubated, the color of the granules changed from white to violet with one breath.

Further modifications and alternative embodiments of the apparatus of this invention will be apparent to those skilled in the art in view of this disclosure. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all this would be apparent to one skilled in the art after having the benefit of this description of the invention.

What is claimed is:

1. An endotracheal device comprising:
  (a) a tubular housing having one end adapted for insertion into a patient's trachea and an other end adapted for placement external of the patient, the housing defining lumen means therethrough from one end to the other end for allowing bidirectional passage of air into and out of the patient to ventilate the patient's lungs; and
  (b) colorimetric carbon dioxide indicator means mounted within the lumen means for determining the presence of carbon dioxide therein while still permitting unimpeded bidirectional flow of air therethrough to ventilate the patient's lungs.

2. The device of claim 1 wherein said housing and indicator means are sterile, and further comprising a removable wrapper enclosing said housing, said wrapper adapted for maintaining said housing in a sterile condition pending use.

3. An endotracheal device comprising:
  (a) a first tubular housing having a first and second end, the first end adapted for insertion into a patient's trachea and the second end adapted for placement external of the patient, the first tubular housing defining lumen means therethrough from the first end to the second end;
  (b) a second housing attached to the second end of the first tubular housing, said second housing defining lumen means therethrough communicating with and forming an extension of the lumen means of the first housing, the lumen means of both housings for allowing bidirectional passage of air into and out of the patient to ventilate the patient's lungs; and
  (c) colorimetric carbon dioxide indicator means mounted within the lumen means of said second housing for determining the presence of carbon dioxide therein while still permitting unimpeded bidirectional flow of air through the housings to ventilate the lungs of the patient.

4. The endotracheal device of claim 3 wherein said housings and indicator means are sterile, and further comprising a removable wrapper enclosing said housings, said wrapper adapted for maintaining said housing in a sterile condition pending use.

5. The endotracheal device of claim 1 or claim 3 further comprising gas permeable membrane means covering said carbon dioxide indicator means for adhering the indicator means to the surface of the lumen means and for preventing the indicator means from entering passing air.

6. The endotracheal device of claim 1 of claim 3 further including a recess defined in the surface of the lumen means having said indicator means mounted therein.

7. The endotracheal device of claim 1 or claim 3 wherein said indicator means comprises a colorimetric carbon dioxide indicator substance and solid support means for supporting the indicator substance while still permitting unimpeded bidirectional flow of air through the lumen means.

8. The endotracheal device of claim 3 wherein said second housing comprises a tubing connector having a passage therethrough which defines the housing lumen means, and the indicator means is mounted within the passage of the connector.

9. The endotracheal device of claim 8 wherein said connector comprises an elbow joint, u-joint or in-line connector.

10. A kit comprising components which are capable of being assembled to provide a device for maintaining an open air passage into and out of a patient's trachea, the components including:
  (a) a first tubular housing having a first and second end, the first end adapted for insertion into the patient's trachea and the second end adapted for placement external of the patient, the first tubular housing defining lumen means therethrough from the first end to the second end;
  (b) a second housing adapted to attach to the second end of the first tubular housing, said second housing defining lumen means therethrough which, when said second housing is attached to the first housing, communicates with and forms an extension of the lumen means of the first housing, the lumen means of both housings allowing bidirectional passage of air into and out of the patient to ventilate the patient's lungs; and (c) colorimetric carbon dioxide indicator means mounted within the lumen means of said second housing for determining the presence of carbon dioxide therein while still permitting unimpeded bidirectional flow of air through the housings to ventilate the patient's lungs.

11. The kit of claim 10 wherein said housings and indicator means are sterile, and further comprising a removable wrapper enclosing said housing, said wrapper adapted for maintaining said housings in a sterile condition pending use.

12. The kit of claim 10 further comprising gas permeable membrane means covering said carbon dioxide indicator means for adhering the indicator means to the surface of the lumen means and for preventing the indicator means from entering passing air.

13. The kit of claim 10 further including a recess defined in the surface of the lumen means with said indicator means mounted therein.

14. The kit of claim 10 wherein said indicator means comprises a colorimetric carbon dioxide indicator substance and solid support means for supporting the indicator substance while still permitting unimpeded bidirectional flow of air through the housings.

15. The kit of claim 10 wherein said second housing comprises a tubing connector having a passage therethrough which defines the housing lumen means, and said indicator means is mounted within the passage of the connector.

16. The kit of claim 15 wherein the tubing connector comprises an elbow joint, u-joint or in-line connector.

17. A device for use in connection with an endotrachael tube for maintaining an open air passage into and out of a patient's trachea, the endotracheal tube having a first and second end, the first end of the endotracheal tube being adapted for insertion into the trachea, and the second end adapted for placement external of the patient, the endotracheal tube defining lumen means therethrough from the first end to the second end, the device comprising:
  (a) a housing having means for attaching to the second end of such an endotracheal tube, said housing defining lumen means therethrough which, when said second housing is attached to the endotracheal tube, communicates with and forms an extension of the lumen means of the endotracheal tube, the lumen means of the endotracheal tube and housing allowing bidirectional passage of air into and out of the patient to ventilate the patient's lungs; and
  (b) colorimetric carbon dioxide indicator means mounted within the lumen means of said housing for determining the presence of carbon dioxide therein while still permitting unimpeded bidirectional flow of air through the housing and endotracheal tube to ventilate the patient's lungs.

18. The device of claim 17 wherein said housing and indicator means are sterile, and further comprising a removable wrapper enclosing said housing, said wrapper adapted for maintaining said housing in a sterile condition pending use.

19. The device of claim 17 further comprising a gas permeable membrane means covering said indicator means for adhering the indicator means to the surface of the lumen means and for preventing the indicator means from entering passing air.

20. The device of claim 17 further including a means defined in the surface of the lumen means and said indicator means is mounted in the recess.

21. The device of claim 17 wherein said indicator means comprises a colorimetric carbon dioxide indicator substance and solid support means for supporting the indicator substance while still permitting unimpeded bidirectional flow of air through the lumen means.

22. The device of claim 17 wherein said housing comprises a tubing connector having a passage therethrough which defines the housing lumen means, and the indicator means is mounted within the passage of the connector.

23. The device of claim 22 wherein the connector comprises an elbow joint, u-joint or in-line connector.

24. The device of claim 1, 3 or 17, or kit of claim 28, wherein said colorimetric carbon dioxide indicator means comprises a carbon dioxide indicator containing hydrazine.

25. A carbon dioxide detector device for use in connection with an endotracheal tube, the endotracheal tube having a first and second end, the first end of the endotracheal tube being adapted for insertion into a patient's trachea, and the second end adapted for placement external of the patient, the endotracheal tube defining lumen means therethrough from the first end to the second end, the device comprising:
  (a) a housing having means for attaching to the second end of the endotracheal tube and defining lumen means therethrough which, when said housing is attached to the endotracheal tube, communicates with and forms an extension of the lumen means of the endotracheal tube, the lumen means of the endotracheal tube and housing allowing bidirectional passage of air into and out of the patient to ventilate the patient's lungs; and
  (b) a colorimetric carbon dioxide indicator substance and solid support means mounted within the lumen means of the housing for supporting the indicator substance while still permitting unimpeded bidirectional flow of air through the lumen means.

26. The device of claim 25 wherein said colorimetric carbon dioxide indicator contains hydrazine.

* * * * *

UNITED STATES PATENT AND TRADEMARK OFFICE
CERTIFICATE OF CORRECTION

PATENT NO. : 4,879,999

DATED : November 14, 1989

INVENTOR(S) : Leiman et al.

It is certified that error appears in the above-identified patent and that said Letters Patent is hereby corrected as shown below:

Column 7, line 52, "an other" should read --another--.

Column 10, line 13, "means" should read --recess--.

Column 10, line 28, "28" should read --10--.

Signed and Sealed this

First Day of January, 1991

Attest:

HARRY F. MANBECK, JR.

*Attesting Officer*  *Commissioner of Patents and Trademarks*

REEXAMINATION CERTIFICATE (2792th)

United States Patent [19]
Leiman et al.

[11] B1 4,879,999
[45] Certificate Issued Feb. 6, 1996

[54] DEVICE FOR THE DETERMINATION OF PROPER ENDOTRACHEAL TUBE PLACEMENT

[75] Inventors: Basil C. Leiman; Bruce D. Butler; Jeffrey Katz; Henry H. Salzarulo, all of Houston, Tex.

[73] Assignee: Nellcor, Inc., Hayward, Calif.

Reexamination Request:
No. 90/003,808, Apr. 26, 1995

Reexamination Certificate for:
Patent No.: 4,879,999
Issued: Nov. 14, 1989
Appl. No.: 58,830
Filed: Jun. 5, 1987

Certificate of Correction issued Jan. 1, 1991.

Related U.S. Application Data

[63] Continuation of Ser. No. 844,090, Mar. 26, 1986, abandoned.
[51] Int. Cl.$^6$ .............. A61M 16/00; A61B 5/08
[52] U.S. Cl. .............. 128/207.14; 128/202.22; 128/719
[58] Field of Search .............. 128/200.26, 202.22, 128/205.23, 207.14–207.16, 656–658, 716, 719; 604/280; 116/200, 201, 206, 209; 422/55–59, 61, 84–89, 103–104; 436/133

[56] References Cited

U.S. PATENT DOCUMENTS

3,667,475  6/1972  Venturelli et al. .

OTHER PUBLICATIONS

"A New Intratracheal Catheter", A. E. Guedel, M.D., Anesthesia and Analgesia, Jul.–Aug., 1928.

"Advantages and Technique of Carbon Dioxid Filtration with Inhalation Anesthesia", R. M. Waters, M.D., Anesthesia and Analgesia, Jun., 1926.

"Carbon Dioxide Absorption", J. Adriani, M.D., The Chemistry and Physics of Anesthesia, Second Edition, 1946 and 1962.

"Design and Function of Pediatric Anesthesia Systems", R. M. Smith, M.D., Anesthesia for Infants and Children, Fourth Edition, 1980.

*Primary Examiner*—Randall L. Green

[57] ABSTRACT

Disclosed is an endotracheal device provided with a colorimetric carbon dioxide indicator. The device functions to indicate the proper intratracheal placement of an endotracheal tube by detecting for the presence of carbon dioxide in expired air passing through the device.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–26 is confirmed.

* * * * *